(12) United States Patent
Al-Shahrani et al.

(10) Patent No.: US 8,501,999 B2
(45) Date of Patent: Aug. 6, 2013

(54) HYDROCARBON RECOVERY FROM SULFONES FORMED BY OXIDATIVE DESULFURIZATION PROCESS

(75) Inventors: Farhan M. Al-Shahrani, Dhahrah (SA); Tiancun Xiao, Marston (GB); Huahong Shi, Oxford (GB); Malcolm L. H. Green, Oxford (GB)

(73) Assignees: Saudi Arabian Oil Company, Dhahran (SA); The Chancellor, Masters and Scholars of the University of Oxford, Oxford (GB)

( * ) Notice: Subject to any disclaimer, the term of this patent is extended or adjusted under 35 U.S.C. 154(b) by 95 days.

(21) Appl. No.: 12/939,598

(22) Filed: Nov. 4, 2010

(65) Prior Publication Data

US 2011/0213187 A1 Sep. 1, 2011

Related U.S. Application Data

(60) Provisional application No. 61/259,121, filed on Nov. 7, 2009.

(51) Int. Cl.
*C07C 37/01* (2006.01)
*C07C 37/04* (2006.01)

(52) U.S. Cl.
USPC .......................................... 568/759; 568/800

(58) Field of Classification Search
USPC .......................................... 568/759, 762, 800
See application file for complete search history.

(56) References Cited

U.S. PATENT DOCUMENTS

| | | | |
|---|---|---|---|
| 3,505,210 | A | 4/1970 | Wallace |
| 3,816,301 | A | 6/1974 | Sorgenti |
| 3,970,545 | A | 7/1976 | Yoo et al. |
| 4,002,727 | A | 1/1977 | Sonoda |
| 5,520,897 | A | 5/1996 | Rogers |
| 5,858,212 | A | 1/1999 | Darcy |
| 6,827,845 | B2 | 12/2004 | Gong |
| 2005/0150819 | A1 | 7/2005 | Wachs |
| 2006/0138029 | A1 | 6/2006 | Malek |
| 2009/0065399 | A1 | 3/2009 | Kocal et al. |
| 2009/0075131 | A1 | 3/2009 | Katsuno |

FOREIGN PATENT DOCUMENTS

WO 03/074633 A1 9/2003

OTHER PUBLICATIONS

LaCount et al., Journal of Organic Chemistry (1977), 42(16), p. 2751-2754.*
T.J. Wallace et al., Tetrahedron (1968), 24, p. 1311-1322.*
Ali, M.F. et al.; Deep desulphurization of gasoline and diesel fuels using non-hydrogen consuming techniques; Fuel, vol. 85, Issues 10-11, Jul.-Aug. 2006, pp. 1354-1363.
Al-Shahrani, F, et al.; Desulfurization of diesel via the H202 oxidation of aromatic sulfides to sulfones using a tungstate catalyst; Applied Catalysis B: Environmental, vol. 73, Issues 3-4, May 11, 2007, pp. 311-316.
Fields, E.K. et al.; Pyrolysis and Mass Spectrum of Dibenxothiophene 5,5 Dioxide; J. Am. Chem. Soc., Jun. 1966, pp. 2836-2837.
Varga, T.R., et al.; Desulfuration of Aromatic Sulfones with Fluorides in Supercritical Water; Energy & Fuels, 18 (2004), pp. 287-288.
Squires, Thomas G. et al.; Preparation, characterization, and flash vacuum pyrolysis of dibenz[c,e][1,2]oxathiin 6-oxide (biphenylene sultine); Journal of Organic Chemistry, vol. 46, No. 11, May 1, 1981, pp. 2373-2376.
Ol'Khivik V.K. et al.; Synthesis and Properties of 4,4'-Bis[5-alkyl(aryl)benzoxazol-2-y1]-2-hydroxy(alkoxy)byphenyl; Russian Journal of Organic Chemistry, vol. 42., No. 8, 2006, pp. 1164-1168.
Supplementary European Search Report, Mar. 25, 2013, European Patent Office Application No. 10829070.1.

* cited by examiner

*Primary Examiner* — Brian J Davis
(74) *Attorney, Agent, or Firm* — Abelman, Frayne & Schwab

(57) ABSTRACT

The process provided herein is concerned with recovery of hydrocarbons from sulfones using an individual alkali and alkaline-earthy base and a mixture of thereof. As the starting materials are sulfones generated by ODS and commercially inexpensive alkali and alkaline-earth bases, the cost and ecological impact of solid waste disposal is minimized.

40 Claims, 10 Drawing Sheets

GC of DBT sulfone (top) and [1,1'-biphenyl]-2-ol (bottom)

GC of 4-MDBT(top), 4-MDBT sulfone(middle) and hydrocarbon phenols(bottom)

GC of 4,6-DMDBT(top), 4,6-DMDBT sulfone(middle) and hydrocarbon phenols(bottom)

GC of mixed sulfurs(top), mixed sulfones(middle) and mixed phenols(bottom,hydrocarbon recovery)

GC spectrum and assignment of 1st batch of mixed sulfones from diesel

GC data and assignment of 2nd batch mixed sulfones from diesel

GC comparison of Batches 1 and 2

GC data and assignment of mixed phenols from Batch 2

GC of mixed sulfones(top) and mixed phenols(bottom) from diesel

HYDROCARBON RECOVERY FROM SULFONES FORMED BY OXIDATIVE DESULFURIZATION PROCESS

RELATED APPLICATIONS

This application claims the benefit of U.S. Provisional Patent Application No. 61/259,121 filed Nov. 7, 2009, the disclosure of which is hereby incorporated by reference.

BACKGROUND OF THE INVENTION

1. Field of the Invention

This invention relates to recovery of hydrocarbons from sulfones formed by oxidative desulfurization.

2. Description of Related Art

Conventional hydrodesulfurization (HDS) processes are based on catalytic hydrogenation conducted at a relatively high pressure (about 30 bars to about 80 bars) and temperature (about 270° C. to about 330° C.). Sulfur compounds can be classified into four groups according to their HDS reactivity described by the pseudo-first-order rate constants. See, e.g., X. Ma, K. Sakanishi and I. Mochida, Hydrodesulfurization reactivities of various sulfur compounds in diesel fuel. *Ind. Eng. Chem.,* 1994, 33, 218; X. Ma, K. Sakanishi, T. Isoda and I. Mochida, Hydrodesulfurization reactivities of narrow-cut fractions in a gas oil. *Ind. Eng. Chem. Res.,* 1995, 34, 748. These groups are:

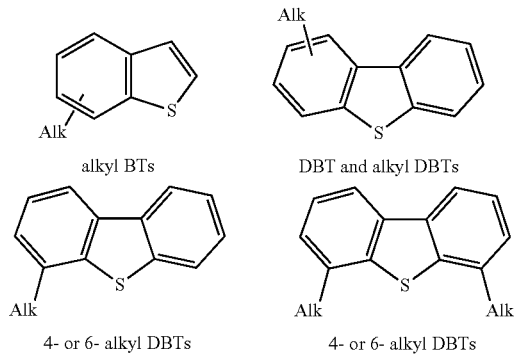

alkyl BTs    DBT and alkyl DBTs 4- or 6- alkyl DBTs    4- or 6- alkyl DBTs

The first group is predominantly alkyl benzothiophenes (BTs); the second, dibenzothiophenes (DBTs) and alkyl DBTs without alkyl substituents at the 4- and 6-positions; the third group, alkyl DBTs with only one alkyl substituent at either the 4- or 6-position; the fourth group, alkyl DBTs with alkyl substituents at the 4- and 6-positions. The sulfur content in the four groups in the is 39, 20, 26 and 15 wt. %, respectively. The relative HDS rate constant for each of the four groups is 36, 8, 3, and 1, respectively.

When the total sulfur content is reduced to 500 ppmw, the main sulfur compounds remaining in the hydrotreated effluent are the third and fourth groups. When the total sulfur content is reduced to 30 ppmw, the sulfur compounds remaining are only the fourth group sulfur compounds, indicating that the lower sulfur content organosulfur compounds have lower HDS reactivity. See D. D. Whitehurst, H. Farag, T. Nagamatsu, K. Sakanishi and I. Mochida, Assessment of limitations and potentials for improvement in deep desulfurization through detailed kinetic analysis of mechanistic pathways. *Catalysis. Today,* 1998, 45, 299. Additional studies using various straight-run gas oils from different crude oils confirmed the differences in reactivity between different sulfur compounds. See, e.g., J. A. R. van Veen and S. T. Sie, Deep hydrodesulfurization of diesel fuel. *Fuel Process. Technol.,* 1999, 61, 1; H. Schulz, W. Bohringer, F. Ousmanov and F. Waller, Refractory sulfur compounds in gas oils. *Fuel Process. Technol.* 1999, 61, 5.

Further investigations have demonstrated that sulfur compounds remaining in diesel fuels at sulfur level lower than 500 ppmw are dibenzothiophenes with alkyl substituents at the 4- and/or 6-position, and are lower in HDS reactivity. See, e.g., Ma *Ind. Eng. Chem.,* 1994, 33, 218; T. Kabe, A. Ishihara and H. Tajima, Hydrodesulfurization of sulfur-containing polyaromatic compounds in light oil. *Ind. Eng. Chem. Res.,* 1992, 31, 1577; X. Ma, K. Sakanishi and I. Mochida, Hydrodesulfurization reactivites of various sulfur compounds in vacuum gas oil. *Ind. Eng. Chem. Res.,* 1996, 35, 2487; B. C. Gates and H. Topsoe, Reactivities in deep catalytic hydrodesulfurization: challenges, opportunities, and the importance of 4-methyldibenzothiophene and 4,6-dimethyldibenzothiophene. *Polyhedron,* 1997, 16, 3213; X. Ma, Deep hydrodesulfurization of diesel fuel: chemistry and reaction processing design, Ph.D. Thesis, Kyushu University, Japan, 1995; X. Ma, K. Sakanishi, T. Isoda, I. Mochida, Comparison of Sulfided CoMo/Al$_2$O$_3$ and NiMo/Al$_2$O$_3$ catalysts, in: M. L. Occelli, R. Chianelli (Eds.), Hydrodesulfurization of Gas Oil Fractions and Model Compounds, in Hydrotreating Technology for Pollution Control, Marcel Dekker, New York, 1996, 183. Consequently, these species are referred to as refractory sulfur compounds. Both steric hindrance and electronic density factor contribute to the observed low reactivity levels of 4- and 6-substituted DBTs in HDS process. See X. Ma, K. Sakanishi, T. Isoda and I. Mochida, Quantum chemical calculation on the desulfurization reactivities of heterocyclic sulfur compounds. *Energy Fuels,* 1995, 9, 33; M. Daage and R. R. Chianelli, Structure-function relations in molybdenum sulfide catalysts: the rim-edge model. *J. Catal.,* 1994, 194, 414.

Due to the low reactivity of refractory sulfur compounds, HDS can normally reduce the crude oil sulfur content from a few thousand ppmw to nearly 500 ppmw. However, it is not economically viable to remove the remainder of the sulfur content due to the high temperature and pressure requirements.

Compared with conventional catalytic HDS, oxidative desulfurization (ODS) can be performed under mild conditions, i.e., relatively low temperature and under atmospheric pressure conditions. ODS typically uses an oxidizing agent, such as hydrogen peroxide, organic peroxide, peracid and ozone, in addition to an oxidation catalyst. In the oxidation process, the divalent sulfur atom of refractory sulfur compounds (condensed thiophene) is oxidized by the electrophilic addition reaction of oxygen atoms to form the hexavalent sulfur of sulfones. The chemical and physical properties of sulfones are significantly different from those of the hydrocarbons in fuel oil. Therefore, sulfones can be removed by conventional separation methods such as filtration, solvent extraction and adsorption. An effective ODS process, which can decrease sulfur in the transportation fuel from 1100 ppm to 40 ppmw, is described in WO/2007/103440 filed on Mar. 5, 2007 (F. Al-Shahrani, T. Xiao, G. D. Martinie and M. L. H. Green, Catalytic Process For Deep Oxidative Desulfurization of Liquid Transportation Fuels) and in F. Al-Shahrani, T. Xiao, S. A. Llewellyn, S. Barri, Z. Jiang, H. Shi, G. Martinie and M. L. H. Green, *Applied Catalysis B,* V. 73., No. 3-4, p. 311 (2007). ODS is considered a promising substitute or supplement to HDS for deep desulfurization of transportation fuels.

The compositions of common sulfides in fuel oil and their respective sulfones are tabulated in Table 1:

TABLE 1

| | DBT | DBTO$_2$ | 4-MDBT | 4-MDBTO$_2$ | 4,6-DMDBT | 4,6-DMDBTO$_2$ |
|---|---|---|---|---|---|---|
| C H % | 82.58 | 70.36 | 83.81 | 72.16 | 84.88 | 73.76 |
| S % | 17.42 | 14.84 | 16.19 | 13.94 | 15.12 | 13.14 |
| O % | 0 | 14.80 | 0 | 13.90 | 0 | 13.10 |

Sulfides consist of carbon, hydrogen and sulfur. For example, DBT is constituted by 82.58% carbon and hydrogen (hydrocarbon) and 17.42% sulfur. Sulfone consists of carbon, hydrogen, sulfur and oxygen. For example, DBT sulfone is constituted by 70.36% hydrocarbon, 14.84% sulfur and 14.80% oxygen. With alkyl substituted DBT sulfone, the percentage of hydrocarbon increases. For example, hydrocarbons constitute 72.16% of MDBT sulfone and 73.76% of DMDBT sulfone. Sulfones formed by ODS processes from diesel fuel are not a single species, but a very complicated mixture which includes not only DBT sulfone, but also several alkyl substituted DBT sulfones, such as 4-MDBT sulfone, 4,6-DMDBT sulfone, 1,4-DMDBT sulfone, 1,3-DMDBT sulfone, TriMDBT sulfone, TriEDBT sulfone, and C3 DBT sulfone. The structures of these sulfones are given below. The sulfone species may vary with different source of diesel.

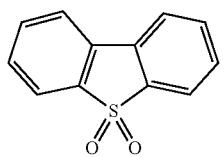
DBT sulfone

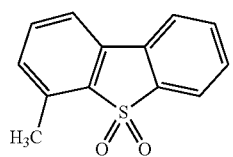
4-MDBT sulfone

-continued

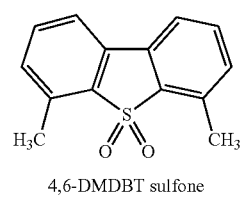
4,6-DMDBT sulfone

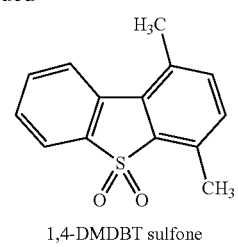
1,4-DMDBT sulfone

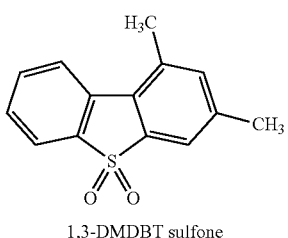
1,3-DMDBT sulfone

TriMDBT sulfone

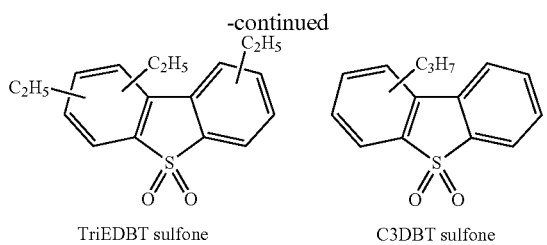
TriEDBT sulfone     C3DBT sulfone

The GC-MS of mixed sulfones from diesel fuel was reported in M. F. Ali, A. Al-Malki, B. El-Ali, G. Martinie and M. N. Siddiqui, *Fuel*, 2006, 85, 1354, and is presented in FIG. 1. From this data, it is clear that (1) the sulfones from diesel fuel are an extremely complicated mixture; (2) most of the sulfones are alkyl substituted DBT sulfones; (3) the highest percentage is 4,6-DMDBT sulfone; (4) non-substituted DBT sulfone is only a very small percentage; and (5) there remain some alkyl substituted DBT sulfones that are difficult to completely identify.

Unlike HDS, in which hydrogenated products remain with fuel oil and organic sulfur is converted into gaseous H$_2$S that leave the fuel oil mixture, sulfones formed by ODS must be separated and removed. Since hydrocarbons constitute more than 70% of a sulfone compound, separation and removal of sulfone will inevitably cause hydrocarbon yield loss in the fuel oil product and generation of solid waste. Generation of 1 g of sulfone will cause a loss of more than 0.7 g of hydrocarbon from. In an ODS process, for 1 million tons of diesel containing 500 ppme sulfur, based on DBT only, 2870 tons of DBT will be lost and 3368 tons of DBT sulfone will be generated. If the calculation is based on only 4-MDBT 3088 tons of 4-MDBT (0.31%) will be lost and 3586 tons of 4-MDBT sulfone will be generated. If the calculation is based on only 4,6-DMDBT, the loss of hydrocarbon and generation of sulfone will both increase. Table 2 details these calculations for the loss of hydrocarbon and generation of sulfones based on 1 million tons of diesel containing 500 ppme sulfur.

TABLE 2

| Name | Diesel | S | DBT | DBTO$_2$ | 4-MDBT | 4-MDBTO$_2$ | 4,6-DMDBT | 4,6-DMDBTO$_2$ |
|---|---|---|---|---|---|---|---|---|
| Amount (tons) | 10$^6$ | 500 | 2870 | 3368 | 3088 | 3586 | 3307 | 3805 |
| % | 100 | 0.05 | 0.29 | 0.34 | 0.31 | 0.36 | 0.33 | 0.38 |

Therefore, recovery of hydrocarbons from sulfones generated by ODS is an important step to reduce hydrocarbon yield loss and to avoid the increased cost of solid waste disposal. Furthermore, recovery of hydrocarbons from sulfones generated by ODS can enhance the desirability of using ODS for oil refining.

Various attempts have been made to recover hydrocarbons from DBT sulfone. These include pyrolysis, decomposition in the presence of alkali in an organic solvent, decomposition in the presence of alkali in water, and decomposition in the presence of potassium fluoride in the presence of supercritical water.

Direct decomposition of dibenzothiophene sulfone was studied by Fields and Meyerson (E. K. Fields and S. Meyerson, *J. Am. Chem. Soc.*, 1966, 88, 2836). Pyrolysis of DBT sulfone was conducted at 690° C. with a contact time of 15 seconds was reported provide a 95% yield of a 6:1 mixture of dibenzofuran and dibenzothiophene:

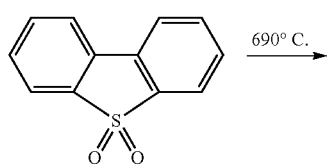

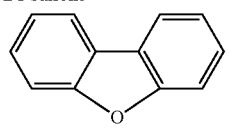 + 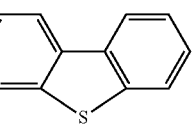

dibenzofuran  dibenzothiophene

Wallace and Heimlich (T. J. Wallace and B. N. Heimlich, *Tetrahedron*, 1968, 24, 1311) studied the mechanism of reaction for alkali decomposition of DBT sulfone and related compounds in white oil as an organic solvent. The results of alkali decomposition indicated that the stability of the DBT nucleus is markedly dependent on the oxidation state of the S-atom. The products formed in the decomposition reaction vary with temperature, contact time, and the initial ratio of base to dioxide. They observed the formation of 18% sodium-2-phenylbenzenesulfonate, 5.8% sodium-2-phenylphenolate, 2% biphenyl and 19.5% dibenzofuran when DBT sulfone was treated with sodium hydroxide in white oil at 300° C. for 4 h. After a similar treatment for 5.5 h, only sulfur-free products, 5% biphenyl and >90% dibenzofuran, were observed:

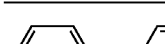

Table 3 shows the of decomposition of DBT sulfone under various reaction conditions in white oil.

Lacourt and Friedman (R. B. Lacount and S. Friedman, *J. Org. Chem.*, 1977, 42, 2751) reported the decomposition reaction of DBT sulfone in excess aqueous alkali (NaOH) at 300° C. in an autoclave. After acidification, 2-phenylphenol was obtained as the only organic compound and sodium sulfite was confirmed in the water layer as shown below:

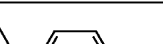

Calcium oxide and sodium carbonate were also used for comparison, as shown in Table 4.

TABLE 4

| Base | Base/DBT sulfone(mol) | Temp. °C. | Time/h | 2-phenylphenol, % | Sulfone recovered % |
|---|---|---|---|---|---|
| NaOH | 5 | 300 | 5 | 100 | 0 |
| NaOH | 5 | 300 | 1 | 99 | 0 |
| NaOH | 5 | 200 | 1 | 4 | 89 |
| CaO | 5 | 300 | 5 | 15 | 76 |
| $Na_2CO_3$ | 5 | 300 | 5 | 89 | 0 |

Varga et al (T. R. Varga, Y. Ikeda and H. Tomiyasu, *Energy & Fuels*, 2004, 18, 287) reported that hydrocarbon recovery can be accomplished by reaction of sulfones and KF in supercritical water as shown below:

TABLE 3

| | | | | Products, mole % yield | | | |
|---|---|---|---|---|---|---|---|
| Base | Base/DBT sulfone (mol) | Temp. °C. | Time/h | $SO_3K/Na$ | OK/Na | (dibenzofuran) | (biphenyl) |
| KOH | 5 | 200 | 3 | 45.0 | 40.0 | 5.0 | — |
| KOH | 5 | 250 | 1.7 | 47.6 | 50.7 | 1.0 | 3.0 |
| KOH | 5 | 300 | 1/6 | 70.0 | 29.6 | 1.7 | 0.8 |
| NaOH | 5 | 300 | 5.5 | — | — | >90 | ~5 |
| NaOH | 5 | 300 | 4 | 18.0 | 58.0 | 19.5 | 2.0 |
| None | — | 300 | 23 | | No reaction | | |

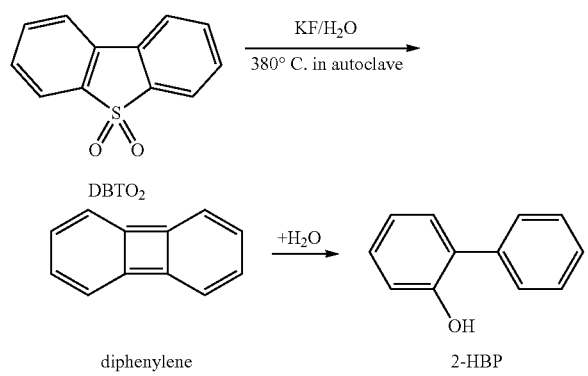

Table 5 below summarizes the researches for hydrocarbon recovery from DBT sulfone as a model compound. There are only a few examples available in the literature.

TABLE 5

Summary of research for hydrocarbon recovery from DBT sulfone

| Reactant | Base | Reaction condition | Products | Notes | Author |
|---|---|---|---|---|---|
| $DBTO_2$ | none | Pyrolysis 690° C. | [dibenzofuran and dibenzothiophene structures] | Desulfur incomplete, temperature too high to realize | Field & Meyerson |
| $DBTO_2$ | NaOH | 300° C. 5.5 h in white oil | [dibenzofuran and biphenyl structures] | Desulfur complete | Wallace & Heimlich |
| $DBTO_2$ | NaOH | 300° C. 5 h in water in autoclave | [2-hydroxybiphenyl structure] | Desulfur complete | Lacourt & Friedman |
| $DBTO_2$ | KF | 380° C. in autoclave, supercritical water | [2-hydroxybiphenyl structure] | Desulfur complete, condition too harsh to realize | Varga et al |

Table 5 indicates that the recovery products are mainly dependent on reaction condition. For pyrolysis, the temperature was up to 690° C. Beside the sulfur-free product dibenzofuran, there was greater than 15% DBT. Further, the very high temperature limits the applicability of this process. For decomposition in white oil, the reaction was carried out under nitrogen at 300° C. There were two different sulfur-free products, dibenzofuran and biphenyl. While there is no requirement for an autoclave, there are few organic solvents that can withstand operating temperatures of 300° C. For decomposition in water, the reaction was run in an autoclave at 300° C. There was only one sulfur-free product, [1,1'-biphenyl]-2-ol/ or 2-phenylphenol. For decomposition under supercritical water conditions, the reaction was run in an autoclave at 380° C. The only product was [1,1'-biphenyl]-2-ol/or 2-phenylphenol.

A major concern with the above-described existing approaches is that hydrocarbon recovery results were based on the commercially available DBT sulfone. However, hydrocarbon recovery from the substituted DBT sulfones or mixtures of these sulfones has not been reported. There is also no report of hydrocarbon recovery from sulfones formed from fuel oil. As shown in FIG. 1, and as discussed above and in the referenced F. Al-Shahrani et al. PCT application, the F. Al-Shahrani 2007 article and the M. F. Ali 2006 article, sulfones formed by ODS of diesel are an extremely complicated mixture, and DBT sulfone represents only a very small percentage of this mixture. Therefore, it is inappropriate to use solely DBT sulfone as the model compound in a study of hydrocarbon recovery from the mixed sulfones formed by ODS. Substituted DBT sulfones are not commercially available alone or as a mixture.

SUMMARY OF THE INVENTION

The process provided herein is concerned with recovery of hydrocarbons from sulfones. Examples are provided below that demonstrate successful hydrocarbon recovery of alkyl substituted DBT sulfones, model mixtures of sulfones, and mixtures of sulfones derived from ODS of diesel.

The processes herein are applicable for the hydrocarbon recovery from a single sulfone, a mixture of sulfones and a mixture of sulfones formed by ODS. This can be accomplished by using an individual alkali and alkaline-earthy base and a mixture of thereof, such as alkali hydroxide, MOH, $M=Li^+, Na^+, K^\alpha, Rb^+, Cs^+$, alkali carbonate, $M_2CO_3$, $M=Li^+, Na^+, K^+, Rb^+, Cs^+$ and alkaline earthy hydroxide, $M(OH)_2$, (in which M is $Mg^{2+}, Ca^{2+}, Sr^{2+}, Ba^{2+}$ or alkali alkoxide), MOR, (in which M is $Li^+, Na^+, K^+, Rb^+, Cs^+$, and R is an alkyl group, such as methyl, ethyl, propyl, butyl, tert-butyl and the like).

As the starting materials are sulfones generated by ODS and commercially inexpensive alkali and alkaline-earth bases, the cost and ecological impact of solid waste disposal is minimized.

Since the products of this process are 2-phenylphenol/or mixture of 2-phenylphenol and alkyl-substituted phenylphenol and inorganic sulfite salt, a process is also provided for generation of a mixture of valuable chemicals which could be used in the pharmaceutical industry or added to diesel as a combustible fuel additive.

In certain embodiments, a process is provided for the hydrocarbon recovery from a single sulfone, a mixture of sulfones and a mixture of sulfones formed by ODS while using substantially no solvent.

In further embodiments a process is provided for the hydrocarbon recovery from a single sulfone, a mixture of sulfones and a mixture of sulfones formed by ODS carried out in a substantially ambient pressure environment.

BRIEF DESCRIPTION OF THE DRAWINGS

The invention will be described in further detail below and with reference to the attached drawings where.

DETAILED DESCRIPTION OF THE INVENTION

Figure 1:
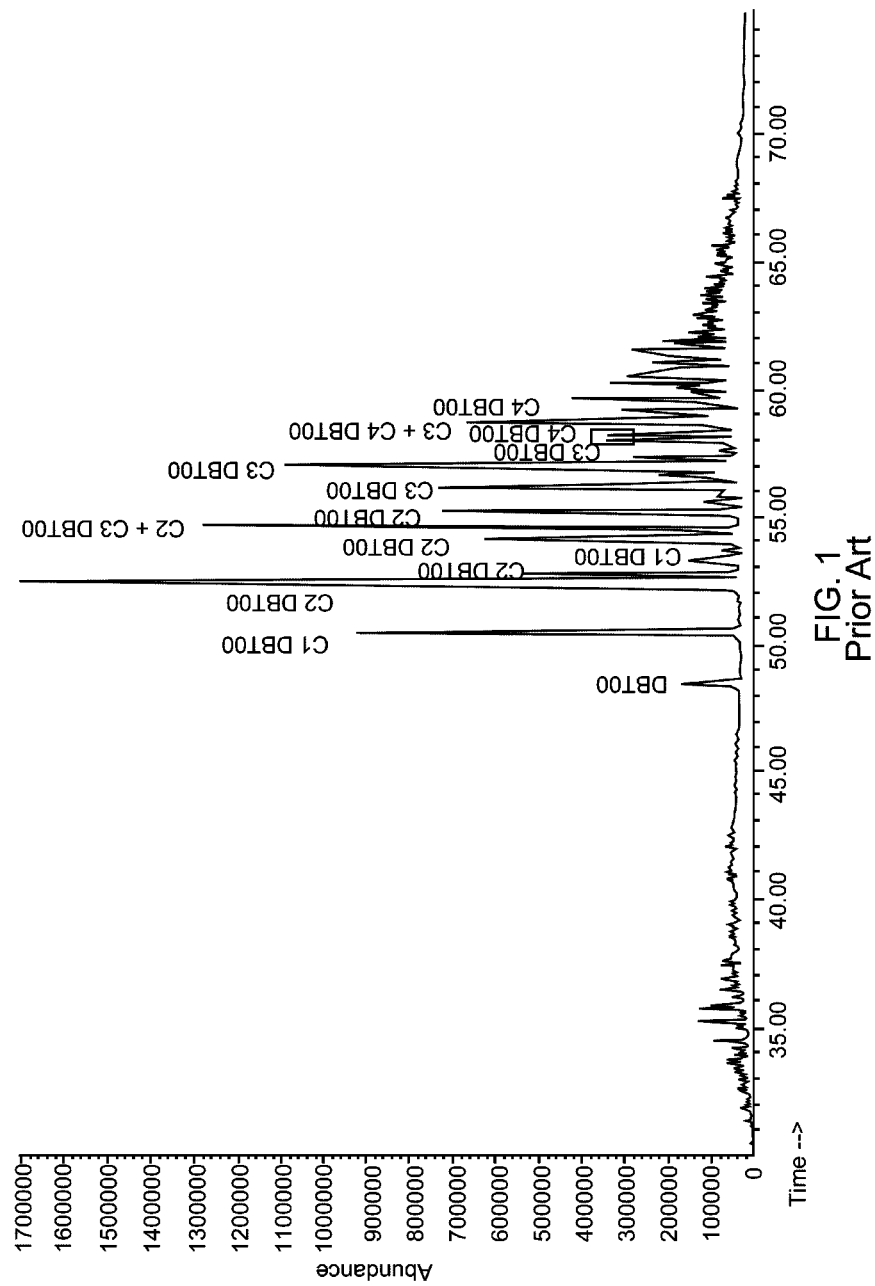
FIG. 1 is a GC spectrum of mixed sulfones from diesel fuel.

The process of the present invention can be applied to various sulfones. In certain embodiments, the sulfones comprise a mixture of sulfones.

One group of sulfones that can be subjected to the hydrocarbon recovery process according to the present invention include alkyl substituted benzothiophene or dibenzothiophene sulfones. These can be mono-substituent, di-substituents or tri-substituents. The alkyl group can be one or more of a methyl group, an ethyl group, a propyl group, or a butyl group. Preferably the alkyls are methyl groups and/or ethyl groups. Representative chemical structures of alkyl substituted benzothiophene or dibenzothiophene sulfones include:

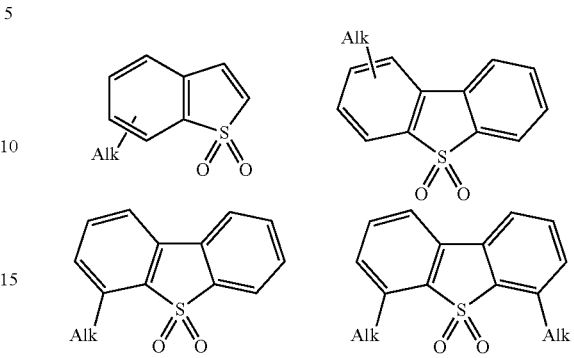

Another group of sulfones that can be subjected to the hydrocarbon recovery process according to the present invention include extended conjugation benzothiophene/dibenzothiophene sulfones, for example:

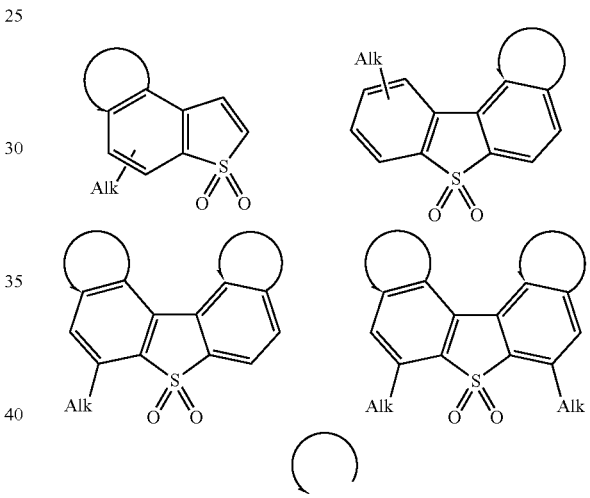

extended aromatic ring

The process of the present invention can be carried out using various alkaline compounds, including alkali hydroxides, alkali carbonates, alkaline earth hydroxides, or mixtures thereof. Exemplary alkali hydroxide include MOH, wherein $M=Li^+, Na^+, K^+, Rb^+,$ or $Cs^+$. Exemplary alkali carbonates include $M_2CO_3$, wherein $M=Li^+, Na^+, K^+, Rb^+,$ or $Cs^+$. Exemplary alkaline earth hydroxides include $M(OH)_2$, wherein $M=Mg^{2+}, Ca^{2+}, Sr^{2+},$ or $Ba^{2+}$.

In certain embodiments, the process further includes adding a dilute acid solution to neutralize the reaction mixture. The acid solution can be acetic acid, hydrochloric acid, sulfuric acid or a mixture thereof. The acid can also be a related inexpensive carboxylic or mineral acid.

EXAMPLES

The invention will be further described in conjunction with the results of tests that are representative of various embodiments. As will be apparent to those of ordinary skill in the art, various modifications and substitutions can be made that are within the scope of the invention. A general description of the laboratory-scale tests follows.

The following examples describe the stepwise procedure for practicing hydrocarbon recovery process of the invention. Also described are tests using both a prepared sample, or model feed, and an actual commercial diesel fraction sample. In these examples, the organic chemicals used in preparing the test compositions were purchased from Aldrich Chemicals Company, Inc. of Milwaukee, Wis., USA, unless otherwise indicated. GC-FID analysis was carried out in Auto System XL Gas Chromatograph commercially available from Perkin Elmer of Waltham, Mass., USA. GC-MS measurement was carried out with Clarus 500 Gas Chromatograph and Mass Spectrometer commercially available from Perkin Elmer. Samples for GC-FID and GC-MS were prepared by dissolving a small amount of testing sample in octane or dichloromethane.

Example 1

0.5 g of DBT sulfone (2.31 mmol), 0.4 g of NaOH (10 mmol) and 5 ml of $H_2O$ were added into a 10 ml autoclave and sealed. It was heated to 300° C. (5° C./min) and dwelled for 1.5 h in a furnace. It was cooled to room temperature and opened with care. The colorless solution was removed by a pipette. The autoclave was washed with $H_2O$. The collected solution was adjusted to pH~7 using a dilute HCl solution. White solid was formed. The mixture was extracted by $CH_2Cl_2$. An organic layer was collected and dried by anhydrous $Na_2SO_4$. The filtration was evaporated to dryness to give 0.34 g (86.5% recovery) of white crystalline solid. GC spectrum (FIG. 2) indicated that the sulfone is completely decomposed and there is only one species in the decomposition product. GC-MS result confirmed that it is [1,1'-biphenyl]-2-ol (MW=170).

[1,1'-biphenyl]-2-ol $C_{12}H_{10}O$, MW: 170.21. GC-MS: 171 (13.2%), 170 (100%), 169 (77.1%), 168 (14.8%), 142 (13.3%), 141 (42.6%), 139 (16.5%), 115 (39.8%), 70 (10.3%), 63 (13.8%).

The water layer was tested by iodine clock reaction which indicated the presence of $SO_3^{2-}$.

The reaction chemistry for Example 1 is as follows:

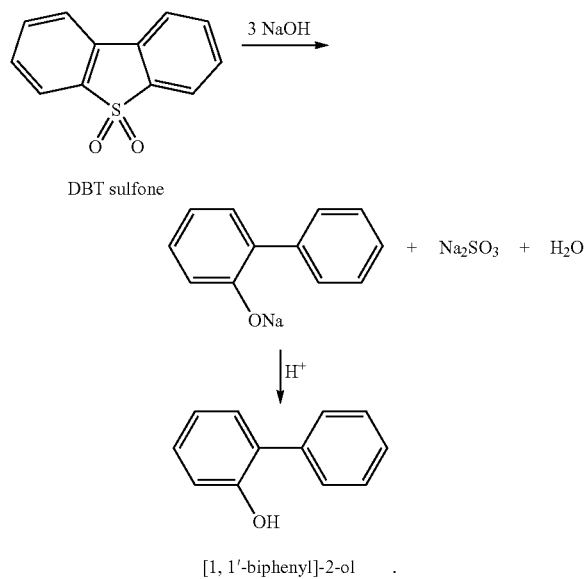

DBT sulfone

[1, 1'-biphenyl]-2-ol

Figure 2:
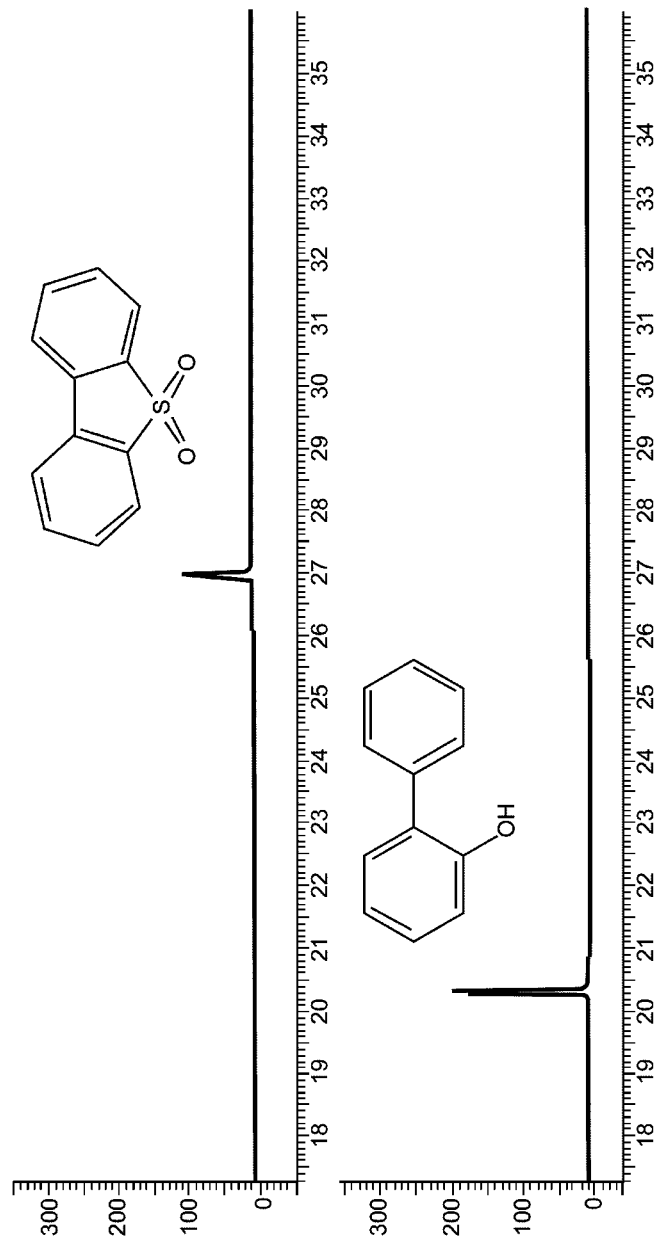
FIG. 2 are GC spectra of DBT sulfone and [1,1'-biphenyl]-2-ol.

FIG. 2 indicated that [1,1'-biphenyl]-2-ol is the only decomposing product from DBT sulfone. This result is in accordance with Lacourt's result discussed above.

When other alkali hydroxides, such as LiOH, KOH, RbOH and CsOH were used, sulfur-free [1,1'-biphenyl]-2-ol was also fully recovered under the same reaction conditions.

For alkaline-earth hydroxides, there were two different results. When $Sr(OH)_2$ and $Ba(OH)_2$ were used, sulfur-free [1,1'-biphenyl]-2-ol was fully recovered after treatment at 300° C. for 5 h in an autoclave. When $Mg(OH)_2$ and $Ca(OH)_2$ were used, more than 90% of DBT sulfone was recovered.

When alkali carbonates, such as $Na_2CO_3$ and $K_2CO_3$ were used, sulfur-free [1,1'-biphenyl]-2-ol was fully recovered after treatment at 300° C. for 5 h in an autoclave.

When alkali alkoxide, such as sodium methoxide and potassium tert-butoxide were used, sulfur-free [1,1'-biphenyl]-2-ol was fully recovered after treatment at 300° C. for 2 h in an autoclave.

Importantly, when NaOH without water as solvent was used, sulfur-free [1,1'-biphenyl]-2-ol was fully recovered after treatment at 300° C. for 2 h in nitrogen atmosphere. This represents the hydrocarbon recovery process can be carried out without using a solvent or an autoclave.

Example 2

The reaction for preparation of 4-MDBT sulfone is shown below:

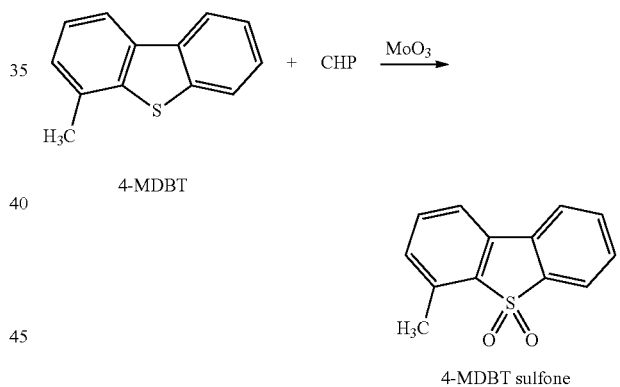

4-MDBT

Figure 3:
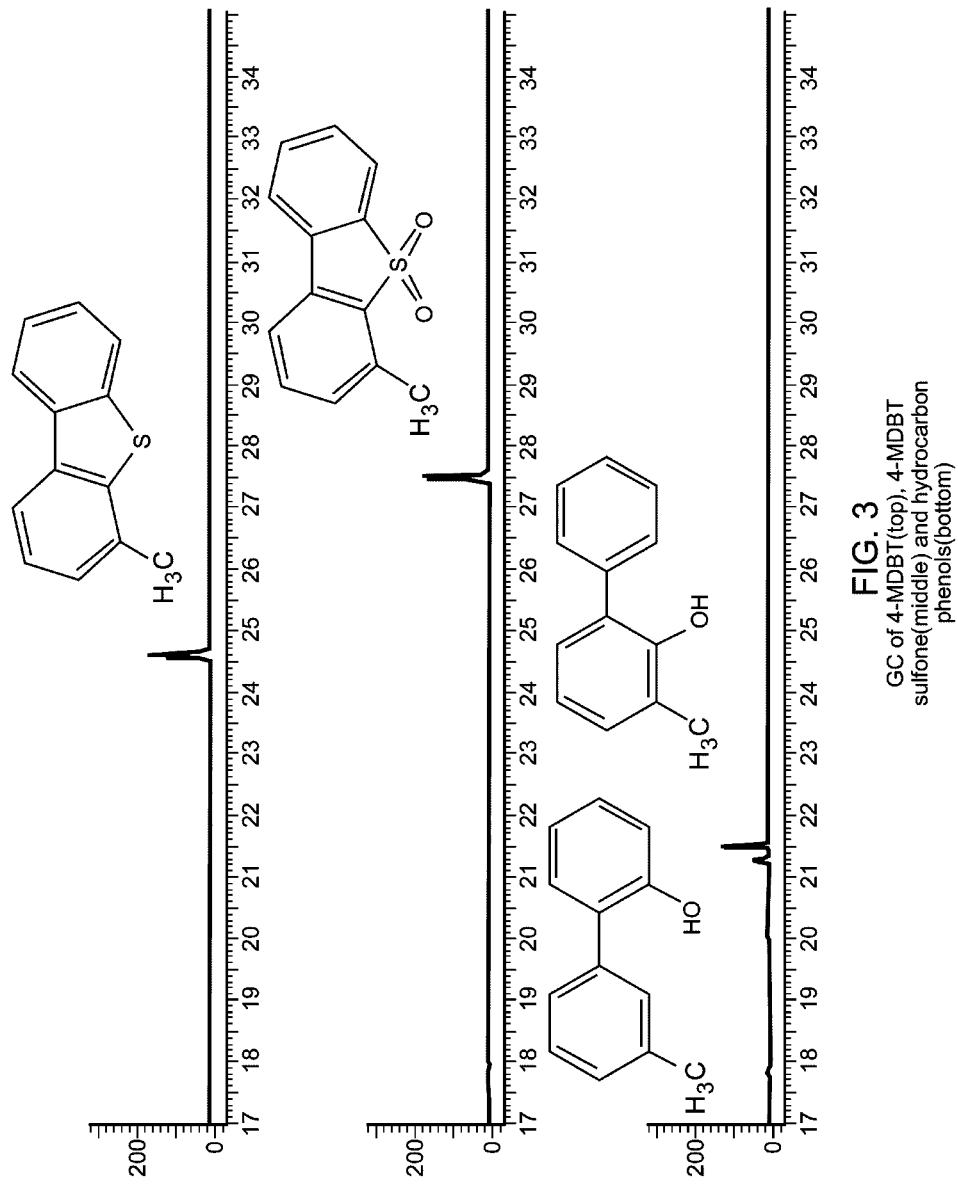
FIG. 3 are GC spectra of 4-MDBT, 4-MDBT sulfone and hydrocarbon phenols.

4-MDBT sulfone 2 g of 4-MDBT (10.09 mmol) was dissolved in 80 ml of octane in a 250 ml round-bottomed flask. 100 mg of $MoO_3$ and 10 ml of cumene hydroperoxide (54.14 mmol) were added. The mixture was heated to 100° C. for 5 h with magnetic stirring. After cooling down to room temperature, large amount of white solid was filtered and washed with hexane. The white solid was dried in air and then dissolved in $CH_2Cl_2$. The insoluble precipitation was filtered and washed with $CH_2Cl_2$. $CH_2Cl_2$ was evaporated to dryness to give 1.81 g (77.9%) of white crystalline solid. GC data (FIG. 3, middle) indicated that there is only one species. GC-MS result confirmed that it is 4-MDBT sulfone.

4-MDBT sulfone $C_{13}H_{10}O_2S$, MW: 230.28. GC-MS: 230 (100%), 201 (29.5%), 187 (25.5%), 181 (36.1%), 165 (21.3%), 152 (20.5%), 139 (20.1%), 136 (29.3%), 115 (20.1%), 63 (19.1%).

The reaction for hydrocarbon recovery from 4-MDBT sulfone is shown below:

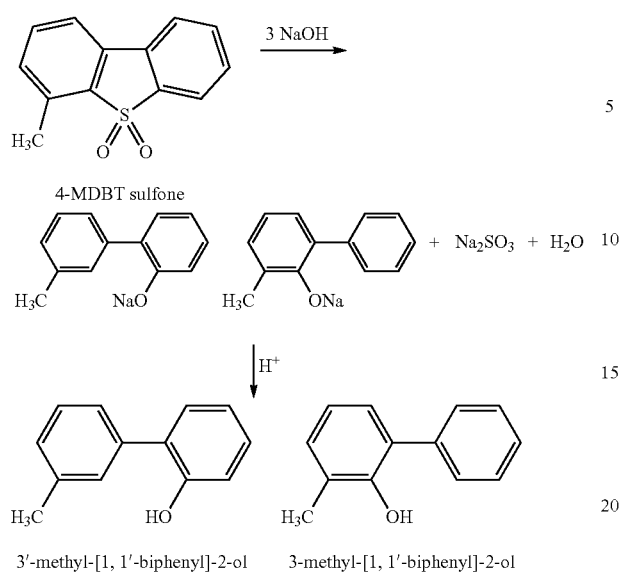

0.5 g of 4-MDBT sulfone (2.17 mmol), 0.4 g of NaOH and 5 ml of H₂O were added in a 10 ml autoclave and sealed. It was heated to 300° C. (5° C./min) and dwelled for 1.5 h in a furnace. The autoclave was cooled to room temperature and opened with care. The pale yellow to colorless solution was removed by a pipette. The autoclave was washed with 10 ml of H₂O and 15 ml of DCM. The collected solution was adjusted to pH~7 using dilute HCl solution. The mixture was extracted by CH₂Cl₂. An organic layer was collected and dried by anhydrous Na₂SO₄. The filtration was completely evaporated to leave pale yellow sticky liquid, 0.35 g (87.5% recovery). GC data (FIG. 3, bottom) indicated that the sulfone is completely decomposed and there are two species in the product. The GC-MS result confirmed that they are isomers which have the same molecular weight (184). The left peak is 3'-methyl-[1',1'-biphenyl]-2-ol and the right peak is 3-methyl-[1,1'-biphenyl]-2-ol.

3'-methyl-[1,1'-biphenyl]-2-ol C₁₃H₁₂O, MW: 184.26. GC-MS: 184 (100%), 183 (50.7%), 182 (39.2%), 181 (35.4%), 165 (16.4%), 152 (20.4%), 115 (18.4%), 91 (15.6%), 77 (15.8%), 76 (17.6%).

3-methyl-[1,1'-biphenyl]-2-ol C₁₃H₁₂O, MW: 184.26. GC-MS: 184 (100%), 183 (34.3%), 182 (22.1%), 181 (23.3%), 169 (62.0%), 165 (19.1%), 152 (16.1%), 141 (17.8%), 115 (23.6%), 91 (23.0%).

Considering the structure of 4-MDBT sulfone, there are two possible different cleavages of C—S bonds as shown below. These two cleavages will therefore produce a mixture of isomeric phenols, 3'-methyl-[1',1'-biphenyl]-2-ol (steric hindrance, less product) and 3-methyl-[1,1'-biphenyl]-2-ol (no steric hindrance, more product).

When other alkali hydroxides, such as LiOH, KOH, RbOH and CsOH were used, sulfur-free 3'-methyl-[1,1'-biphenyl]-2-ol and 3-methyl-[1,1'-biphenyl]-2-ol were also fully recovered under the same reaction conditions.

For alkaline-earth hydroxides, there are two different results. When Sr(OH)₂ and Ba(OH)₂ were used, sulfur-free 3'-methyl-[1,1'-biphenyl]-2-ol and 3-methyl-[1,1'-biphenyl]-2-ol were fully recovered after treatment at 300° C. for 5 h in an autoclave. When Mg(OH)₂ and Ca(OH)₂ were used, more than 90% of 4-MDBT sulfone was recovered.

Example 3

Figure 4:
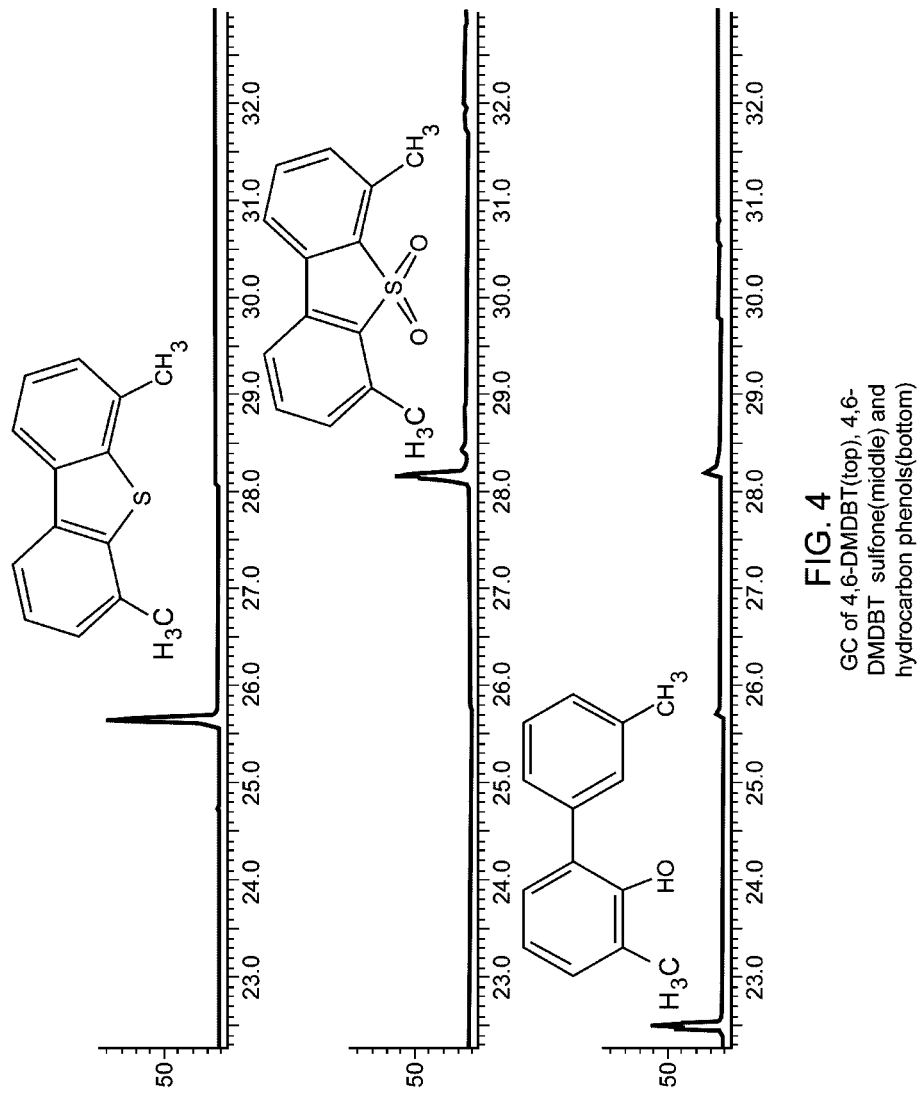
FIG. 4 are GC spectra of 4,6-DMDBT, 4,6-DMDBT sulfone and hydrocarbon phenols.

The reaction for preparation of 4,6-MDBT sulfone is shown below:

400 mg of 4,6-DMDBT (1.88 mmol), 25 ml of octane, 2 ml of CHP (10.8 mmol) and 40 mg of MoO₃ (0.28 mmol) were added into a 100 ml of round-bottomed flask. It was heated to 100° C. for 5 h with magnetic stirring. After cooling down to room temperature, large amount of white solid was filtered and washed with hexane. The white crystalline solid was dried in air and then dissolved in CH₂Cl₂. The insoluble precipitation was filtered and washed with CH₂Cl₂. CH₂Cl₂ was evaporated to dryness to give 0.34 g of white crystalline solid. GC data (FIG. 4 middle) indicated that there are two species in the product. GC-MS result confirmed that the main peak is our expected product 4,6-DMDBT sulfone, and the small peak is incompletely oxidized product 4,6-dimethyldibenzothiophene-5-oxide.

4,6-dimethyldibenzothiophene sulfone C₁₄H₁₂SO₂, MW: 244.31, GC-MS: 244 (100%), 215 (21.2%), 201 (39.7%), 195 (25.6%), 184 (15.8%), 165 (27.6%), 158 (21.1%), 152 (26.2%), 150 (33.7%), 76 (16.3%).

4,6-dimethyldibenzothiophene-5-oxide C₁₄H₁₂SO, MW: 228.31, GC-MS: 228 (28.1%), 213 (16.4%), 212 (100%), 211 (48.7%), 199 (13.8), 197 (19.0%), 185 (20.7%), 152 (14.2%), 105 (28.4%). 92 (20.0%).

The reaction for hydrocarbon recovery from 4,6-DMDBT sulfone is shown below:

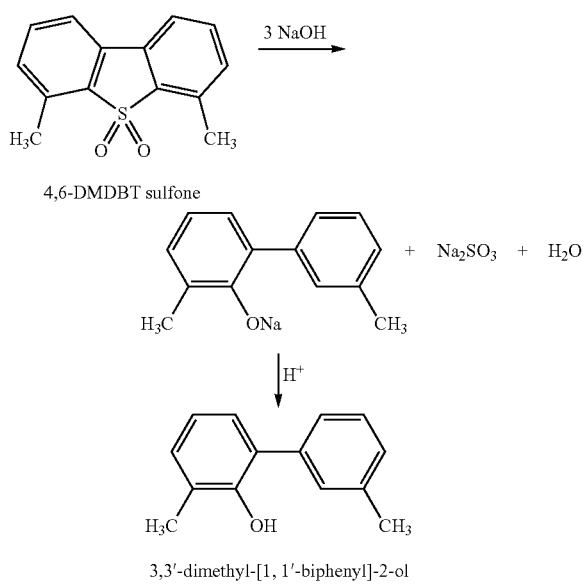

0.3 g of 4,6-DMDBT sulfone (1.23 mmol), 0.2 g of NaOH (5 mmol) and 5 ml of H$_2$O were added in a 10 ml autoclave and sealed. It was heated to 300° C. (5° C./min) and dwelled for 1.5 h in a furnace. The autoclave was cooled to room temperature and opened with care. Pale yellow solution was removed by a pipette. The autoclave was washed with 10 ml of H$_2$O and 15 ml of dichloromethane. The collected solution was adjusted to pH~7 using dilute HCl solution. The mixture was extracted by CH$_2$Cl$_2$. Organic layer was collected and dried by anhydrous Na$_2$SO$_4$. The filtration was completely evaporated to give 0.22 g of brown solid. GC spectrum (FIG. 4 bottom) indicated that there are three species in the product. GC-MS result confirmed that the main peak on the left is the hydrocarbon recovery, 3,3'-dimethyl-[1,1'-biphenyl]-2-ol.

The small peak in the middle is 4,6-dimethyldibenzothiophene and the small peak on the right is un-reacted 4,6-dimethyldibenzothiophene sulfone.

3,3'-dimethyl-[1,1'-biphenyl]-2-ol C$_{14}$H$_{14}$O, MW: 198.26, GC-MS: 199 (14.8%), 198 (100%), 197 (27.4%), 196 (14.8%), 183 (58.2%), 181 (18.7%), 165 (21.9%), 153 (15.0%), 152 (16.2%), 98 (15.5%).

4,6-dimethyldibenzothiophene C$_{14}$H$_{12}$S, MW: 212.31, GC-MS: 213 (17.7%), 212 (100%), 211 (45.9%), 197 (17.2%), 178 (8.1%), 165 (7.6%), 152 (7.5%), 106 (10.8%), 105 (22.0%), 92 (9.8%).

4,6-dimethyldibenzothiophene sulfone C$_{14}$H$_{12}$SO$_2$, MW: 244.31, GC-MS: 244 (100%), 215 (23.6%), 201 (38.3%), 195 (24.7%), 165 (30.5%), 158 (22.4%), 152 (26.7%), 150 (33.1%), 118 (18.5%), 63 (18.4%).

When other alkali hydroxides, such as LiOH, KOH, RbOH and CsOH were used, 3,3'-dimethyl-[1',1'-biphenyl]-2-ol was also fully recovered after treatment at 300° C. for 2 h in an autoclave.

For alkaline-earthy hydroxides, there are two different results. when Sr(OH)$_2$ and Ba(OH)$_2$ were used, 3,3'-dimethyl-[1',1'-biphenyl]-2-ol was fully recovered after treatment at 300° C. for 5 h in an autoclave. But, when Mg(OH)$_2$ and Ca(OH)$_2$ were used, more than 90% of 4,6-DMDBT sulfone was recovered.

Example 4

The reaction for preparation of mixed sulfones of model compounds is shown below:

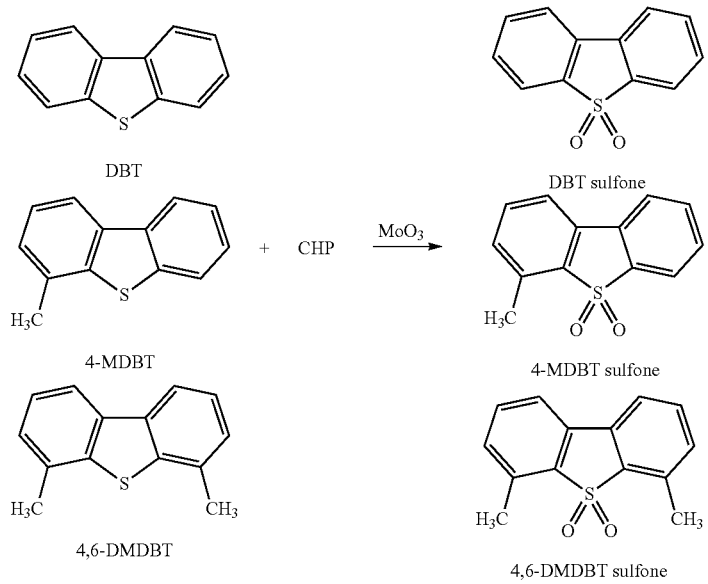

Figure 5:
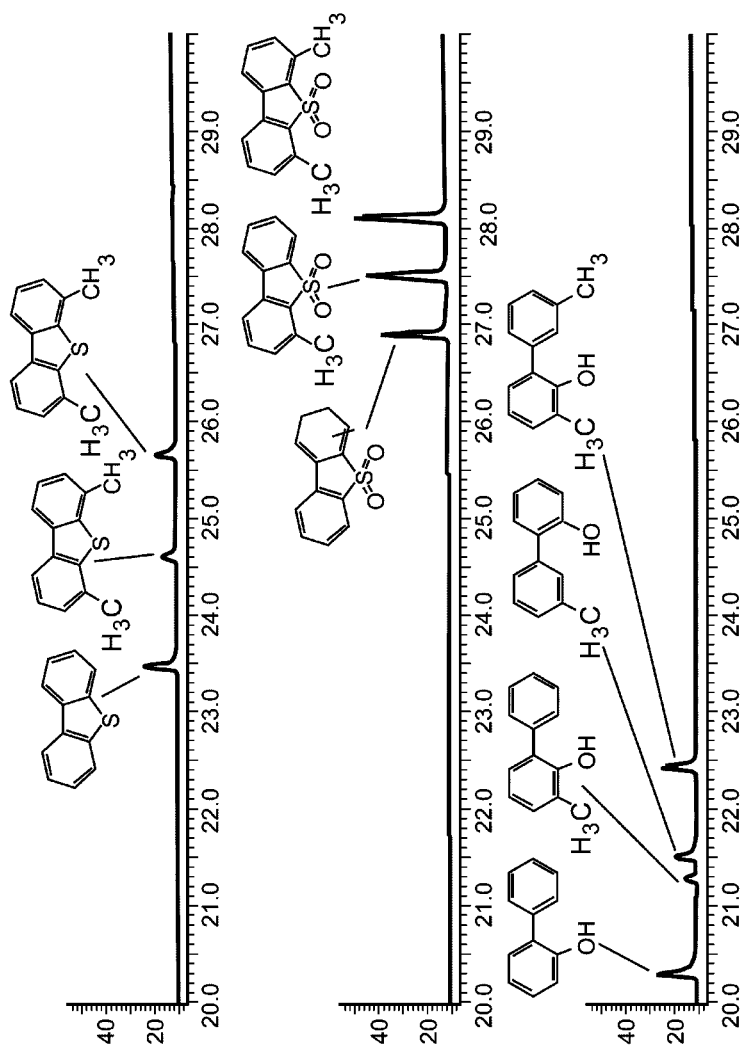
FIG. 5 are GC spectra of GC of mixed sulfurs, mixed sulfones and mixed phenols as a result of hydrocarbon recovery.

200 mg of DBT (1.09 mmol), 200 mg of 4-MDBT (1.01 mmol) and 200 mg of 4,6-DMDBT (0.94 mmol), 100 ml of octane, 100 mg of MoO$_3$ and 3 ml of CHP (16.24 mmol) was added in a 250 ml round-bottomed flask. It was refluxed for 2 h with stirring. After cooling down to room temperature, large amount of white solid was filtered and washed with hexane. The white crystalline solid was dried in air and then dissolved in CH$_2$Cl$_2$. The insoluble precipitation was filtered and washed with CH$_2$Cl$_2$. CH$_2$Cl$_2$ was evaporated to dryness to give 0.59 g of crystalline solid. GC data (FIG. 5 middle) indicated that all the sulfides have been oxidized to their respective sulfones confirmed by GC-MS. The first peak is DBT sulfone. The second peak is 4-MDBT sulfone. The third peak is 4,6-DMDBT sulfone.

Dibenzothiophene sulfone $C_{12}H_8O_2S$, MW: 216.26. GC-MS: 216 (100%), 187 (46.6%), 168 (38.7%), 160 (34.5%), 139 (41.6%), 136 (37.8%), 115 (30.7%), 104 (24.1%), 79 (26.2%), 63 (30.5%).

4-methyldibenzothiophene sulfone $C_{13}H_{10}O_2S$, MW: 230.28. GC-MS: 230 (100%), 201 (31.4%), 187 (28.7%), 181 (35.8%), 165 (21.1%), 152 (20.6%), 136 (34.4%), 115 (21.8%), 69 (21.1%), 63 (21.6%).

4,6-dimethyldibenzothiophene sulfone $C_{14}H_{12}O_2S$, MW: 244.31. GC-MS: 244 (100%), 215 (22.7%), 201 (44.9%), 195 (22.4%), 165 (32.6%), 158 (25.0%), 152 (32.0%), 150 (38.6%), 76 (21.0%), 63 (20.6%).

Below is the reaction for hydrocarbon recovery from mixed sulfones:

3'-methyl-[1,1'-biphenyl]-2-ol $C_{13}H_{12}O$, MW: 184.26. GC-MS: 184 (100%), 183 (97.2%), 182 (35.1%), 181 (28.3%), 165 (32.3%), 152 (23.9%), 115 (26.6%), 77 (20.5%), 69 (22.7%), 55 (28.3%).

3-methyl-[1,1'-biphenyl]-2-ol $C_{13}H_{12}O$, MW: 184.26. GC-MS: 184 (100%), 183 (41.2%), 182 (96.7%), 181 (95.4%), 169 (60.3%), 152 (48.2%), 115 (31.0%), 91 (47.8%), 76 (37.7%), 63 (38.4%).

3,3'-dimethyl-[1,1'-biphenyl]-2-ol $C_{14}H_{14}O$, MW: 198.26, GC-MS: 199 (14.8%), 198 (100%), 197 (30.1%), 196 (69.6%), 195 (49.5%), 183 (58.1%), 181 (26.1%), 165 (30.2%), 152 (29.3%), 115 (24.2%), 97 (20.9%).

When other alkali hydroxides, such as LiOH, KOH, RbOH and CsOH were used, [1,1'-biphenyl]-2-ol, 3'-methyl-[1,1'-biphenyl]-2-ol and 3-methyl-[1,1'-biphenyl]-2-ol, 3,3'-dimethyl-[1',1'-biphenyl]-2-ol were also fully recovered after treatment at 300° C. for 2 h in an autoclave.

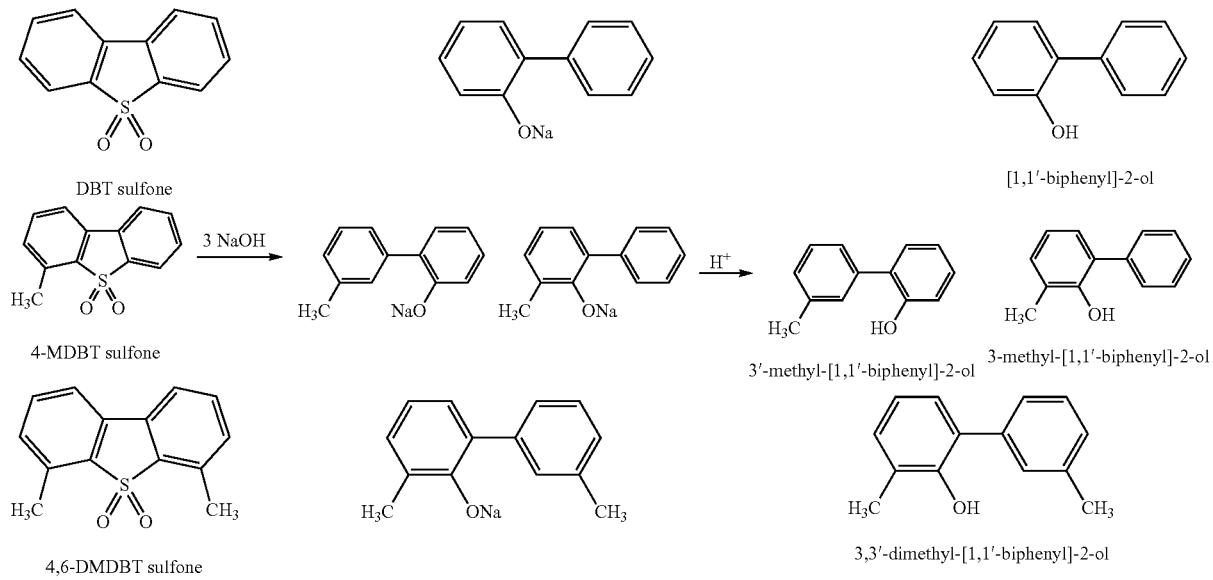

Fig 0.2 g of mixed DBT sulfone, 4-MDBT sulfone, 4,6-DMDBT sulfone, 0.2 g of NaOH and 5 ml of $H_2O$ was added in a 10 ml autoclave and sealed. It was heated to 300° C. (5° C./min) and dwelled for 2 h. The autoclave was cooled to room temperature and opened with care. Colourless solution was removed by a pipette. The autoclave was washed with 10 ml of $H_2O$ and 15 ml of dichloromethane. The collected solution was adjusted to pH~7 using dilute HCl solution. The mixture was extracted by $CH_2Cl_2$. Organic layer was collected and dried by anhydrous $Na_2SO_4$. The filtration was completely evaporated to give a pale yellow sticky liquid 0.15 g. GC spectrum (FIG. 5 bottom) indicated that all sulfones are decomposed to their respective phenols confirmed by GC-MS. The left peak is [1,1'-biphenyl]-2-ol decomposed from DBT sulfone. The middle two peaks is the mixture of phenols, 3'-methyl-[1,1'-biphenyl]-2-ol and 3-methyl-[1,1'-biphenyl]-2-ol, decomposed from 4-MDBT sulfone. The right peak is 3,3'-dimethyl-[1,1'-biphenyl]-2-ol decomposed from 4,6-DMDBT sulfone.

[1,1'-biphenyl]-2-ol $C_{12}H_{10}O$, MW: 170.21. GC-MS: 171 (11.9%), 170 (100%), 169 (78.0%), 168 (51.8%), 142 (13.9%), 141 (42.0%), 139 (26.4%), 115 (41.3%), 69 (10.4%), 63 (15.3%).

For alkaline-earthy hydroxides, there are two different results. When $Sr(OH)_2$ and $Ba(OH)_2$ were used, [1,1'-biphenyl]-2-ol, 3'-methyl-[1,1'-biphenyl]-2-ol and 3-methyl-[1,1'-biphenyl]-2-ol, 3,3'-dimethyl-[1,1'-biphenyl]-2-ol were fully recovered after treatment at 300° C. for 5 h in an autoclave. When $Mg(OH)_2$ and $Ca(OH)_2$ were used, more than 90% of Mixed sulfones was recovered.

Example 5

In a first batch of mixed sulfones formed by ODS of diesel, hydrotreated diesel was subjected to ODS as described in above-referenced WO/2007/103440. A mixture of 300 ml of diesel #2, 30 ml of acetic acid, 1.2 g of $Na_2WO_4 \cdot 2H_2O$ and 5 ml of 30% $H_2O_2$ was added to a round-bottled flask. It was heated to 90° C. for 3 h with continuously magnetic stirring. After cooling to room temperature, two layers formed. The water layer was collected and the oil layer was extracted by 100 ml of 80% methanol. The water layer and extraction were combined. The combination was extracted by $CH_2Cl_2$ twice. The organic layer was collected and dried by anhydrous $Na_2SO_4$. After filtration, most of the $CH_2Cl_2$ was removed. 5 ml of hexane was added and precipitate appeared. The solid was separated by filtration, washed with hexane and dried in air. 50 mg of a brown solid was obtained.

Figure 6:
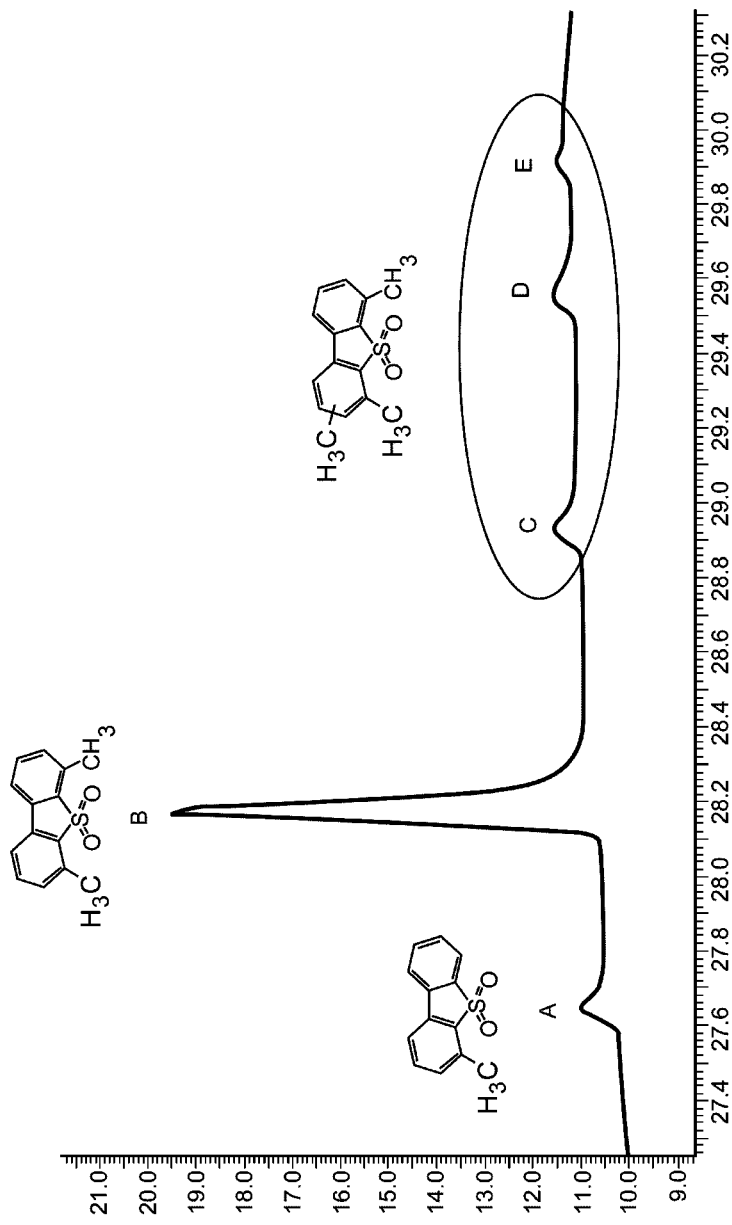
FIG. 6 is a GC spectrum and assignment of a first batch of mixed sulfones from diesel.

GC spectrum (FIG. 6) and GC-MS results indicated that it is a mixture of the compounds 4-methyldibenzothiophene sulfone (A, MW=230), 4,6-dimethyldibenzothiophene sulfone (B, MW=244) and several sulfone analogues. Molecular weights for C, D and E are 258, only one —$CH_3$ more than that of 4,6-DMDBT, but the exact substitution position of the extra —$CH_3$ group was not identified.

A, 4-methyldibenzothiophene sulfone $C_{13}H_{10}O_2S$, MW: 230.28. GC-MS: 230 (100%), 201 (29.8%), 187 (33.3%), 184 (17.5%), 182 (18.7%), 181 (33.9%), 165 (21.1%), 152 (19.3%), 136 (28.5%), 63 (21.3%).

B, 4,6-dimethyldibenzothiophene sulfone $C_{14}H_{12}O_2S$, MW: 244.31. GC-MS: 244 (100%), 215 (21.6%), 201 (39.1%), 195 (24.0%), 184 (15.5%), 165 (28.0%), 158 (21.3%), 152 (26.0%), 150 (32.4%), 76 (16.2%).

C, sulfone $C_{15}H_{14}O_2S$, MW: 258.33. GC-MS: 258 (100%), 244 (39.4%), 207 (22.5%), 201 (30.4%), 195 (28.4%), 179 (32.9%), 178 (29.1%), 165 (31.6%), 152 (24.7%), 150 (21.0%).

D, sulfone $C_{15}H_{14}O_2S$, MW: 258.33. GC-MS: 258 (100%), 215 (51.7%), 209 (23.8%), 207 (48.7%), 179 (18.1%), 178 (18.3%), 165 (22.6%), 152 (18.2%), 150 (53.5%), 73 (19.0%).

E, sulfone $C_{15}H_{14}O_2S$, MW: 258.33. GC-MS: 258 (100%), 215 (38.6%), 207 (41.2%), 179 (31.7%), 178 (36.6%), 172 (24.1%), 165 (24.3%), 152 (18.6%), 150 (20.0%), 89 (15.5%).

Example 6

A second batch of mixed sulfones was also formed. A mixture of 300 ml of diesel #2, 30 ml of acetic acid, 1.2 g of $Na_2WO_4.2H_2O$ and 5 ml of 30% $H_2O_2$ was added in a round-bottled flask. It was heated to 90° C. for 3 h with continuously magnetic stirring. After cooling down to room temperature and addition of 20 ml of water, the mixture was filtered and washed with hexane and water. The solid was dried in air to give 120 mg of a brown solid.

Figure 7:
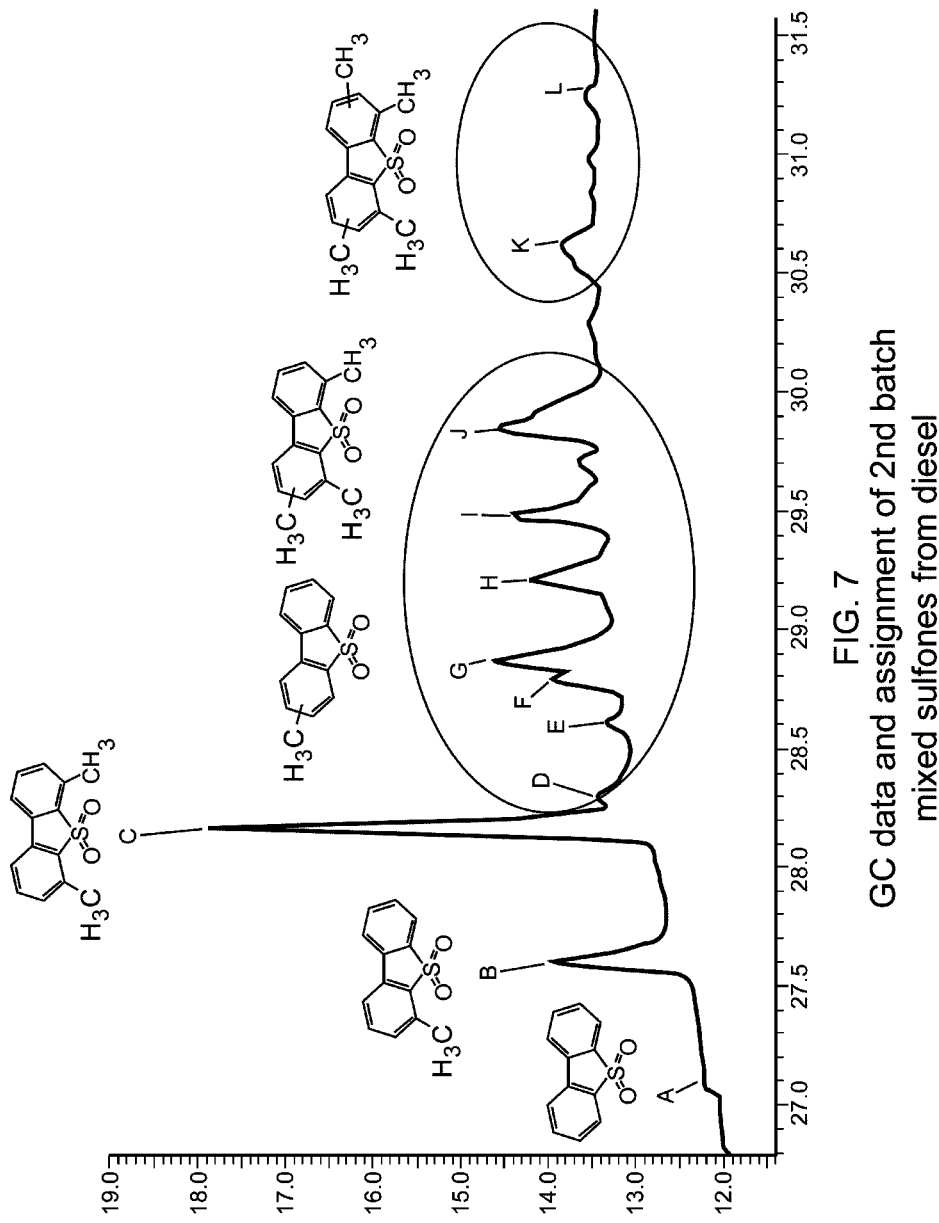
FIG. 7 is a GC spectrum and assignment of second batch of mixed sulfones from diesel FIG. 8 are GC spectra comparing the first and second batches.
Figure 8:
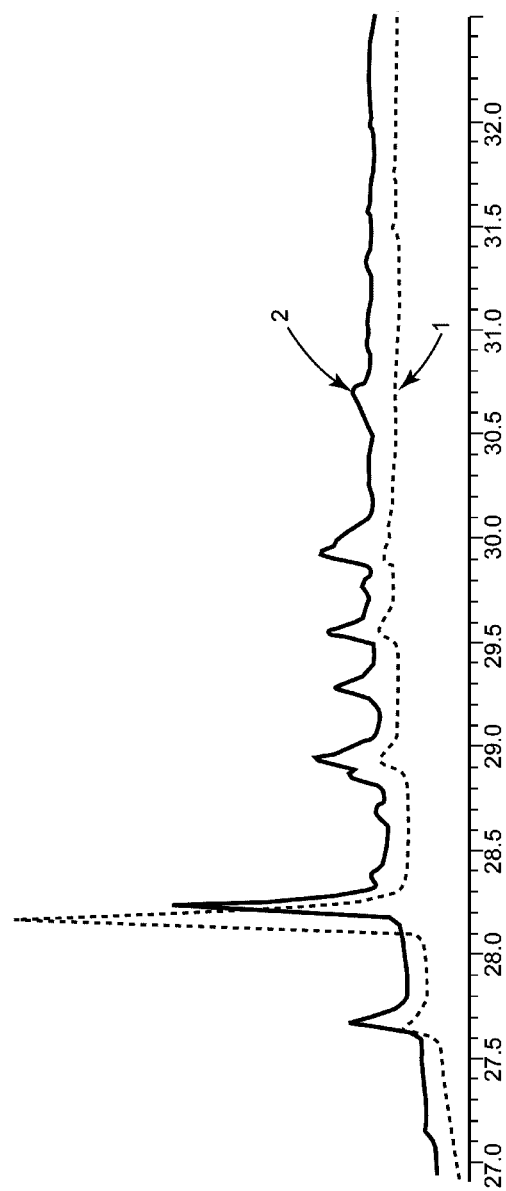

FIG. 7 is the GC spectrum of $2^{nd}$ batch mixed sulfones from diesel #2. GC-MS results indicates that A, B and C are DBT sulfone, 4-MDBT sulfone and 4,6-DMDBT sulfone. D to L can not be accurately assigned, but their molecular weights are all 230, 244, 258 and 272, which mean they are analogues with only —$CH_3$ difference. It is more complicated than that of $1^{st}$ batch of mixed sulfones, since solvents were used for $1^{st}$ batch, and some species of sulfones remained in solvent. For comparison, the GC spectra of $1^{st}$ and $2^{nd}$ batch are presented in FIG. 8.

A, Dibenzothiophene sulfone $C_{12}H_8O_2S$, MW: 216.26. GC-MS: 216 (100%), 207 (95.6%), 187 (50.0%), 168 (50.8%), 160 (40.6%), 139 (57.8%), 136 (44.7%), 79 (41.6%), 63 (40.7%), 57 (48.7%).

B, 4-Methyldibenzothiophene sulfone $C_{13}H_{10}O_2S$, MW: 230.28. GC-MS: 230 (100%), 201 (23.9%), 187 (29.1%), 181 (38.5%), 163 (19.7%), 152 (19.0%), 139 (17.9%), 136 (32.3%), 115 (22.4%), 82 (19.3%).

C, 4,6-Dimethyldibenzothiophene sulfone $C_{14}H_{12}O_2S$, MW: 244.31. GC-MS: 245 (16.9%), 244 (100%), 215 (20.5%), 201 (39.0%), 195 (23.5%), 165 (28.9%), 158 (20.8%), 152 (24.6%), 150 (33.6%), 76 (16.5%).

D, sulfone: 281 (41.3%), 244 (98.3%), 230 (29.0%), 207 (100%), 165 (55.0%), 152 (42.4%), 96 (33.5%), 73 (53.8%), 69 (33.5%), 55 (35.7%).

E, sulfone: 281 (26.3%), 230 (41.7%), 207 (100%), 181 (17.4%), 96 (16.9%), 82 (17.6%), 73 (26.1%), 69 (18.4%), 57 (18.6%), 55 (19.4%).

F, sulfone: 281 (27.0%), 244 (100%), 207 (81.1%), 201 (32.3%), 195 (39.3%), 165 (25.5%), 152 (37.1%), 150 (58.2%), 118 (27.4%), 73 (25.1%).

G, sulfone: 258 (100%), 207 (46.0%), 201 (29.7%), 195 (29.6%), 179 (51.1%), 178 (35.1%), 165 (28.7%), 152 (44.6%), 150 (31.9%), 73 (26.1%).

H, sulfone: 281 (31.3%), 244 (100%), 207 (91.7%), 201 (30.9%), 195 (25.0%), 165 (55.3%), 152 (43.2%), 150 (27.1%), 73 (26.4%), 63 (25.9%).

I, sulfone: 281 (37.0%), 258 (100%), 215 (66.6%), 209 (31.4%), 208 (25.3%), 207 (81.0%), 195 (26.7%), 164 (28.7%), 150 (61.9%), 73 (33.7%).

J, sulfone: 281 (22.0%), 258 (100%), 215 (32.6%), 207 (68.1%), 191 (22.8%), 179 (42.5%), 178 (43.2%), 165 (28.3%), 152 (22.4%), 150 (22.7%).

K, sulfone: 281 (30.3%), 272, 258 (28.8%), 209 (15.4%), 208 (17.4%), 207 (100%), 191 (16.1%), 178 (14.8%), 150 (12.5%), 96 (16.2%), 73 (24.0%).

L, sulfone: 281 (50.7%), 272 (9.8), 209 (12.0%), 208 (15.7%), 207 (100%), 191 (15.4%), 133 (10.9%), 96 (17.9%), 73 (32.1%), 57 (9.3%).

Example 7

Figure 9:
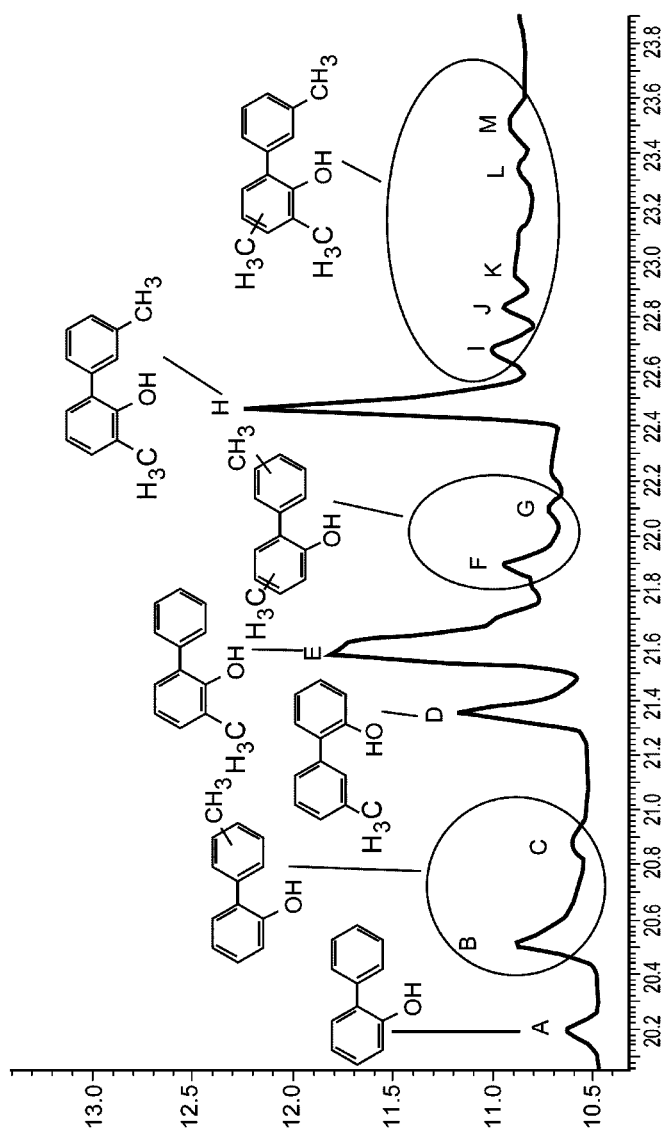
FIG. 9 is a GC spectrum and assignment of mixed phenols from the second batch.

Hydrocarbon recovery from mixed sulfones formed by oxidization of diesel was conducted. 40 mg of $2^{nd}$ batch mixed sulfones, 40 mg of NaOH and 5 ml of $H_2O$ was added in a 10 ml autoclave and sealed. The autoclave was heated to 300° C. (5° C./min) and dwelled for 2 h. The autoclave was cooled to room temperature and opened with care. Pale yellow solution was removed by a pipette. The autoclave was washed with 10 ml of $H_2O$ and 15 ml of dichloromethane. The collected solution was adjusted to pH~7 using dilute HCl solution. The mixture was extracted by $CH_2Cl_2$. Organic layer was collected and dried by anhydrous $Na_2SO_4$. The filtration was completely evaporated to give a pale yellow sticky liquid. GC spectrum (FIG. 9) indicated that all sulfones are decomposed to their respective phenols. The assignments of the mixture can be found in FIG. 9. GC and GC-MS results can help us to assign A, D, E and H peaks as [1,1'-biphenyl]-2-ol (MW=170), 3'-methyl-[1,1'-biphenyl]-2-ol (MW=184), 3-methyl-[1,1'-biphenyl]-2-ol (MW=184) and 3,3'-dimethyl-[1,1'-biphenyl]-2-ol (MW=198). Other peaks are not assigned at this stage, but their molecular weights are 184, 198 and 212, which means they are analogues with only —$CH_3$ difference. This result is in accordance with that of original reactant sulfones described and shown with respect to FIG. 7.

A [1,1'-biphenyl]-2-ol $C_{12}H_{10}O$, MW: 170.21. GC-MS: 171 (10.1%), 170 (100%), 169 (82.0%), 142 (12.3%), 141 (42.2%), 139 (10.6%), 115 (31.8%), 89 (8.0%), 70 (9.6%), 63 (9.1%).

B $C_{13}H_{12}O$, MW: 184.26. GC-MS: 184 (100%), 183 (18.9%), 169 (56.8%), 167 (11.0%), 165 (24.0%), 152 (10.0%), 141 (22.6%), 128 (12.8%), 115 (19.3%), 82 (20.2%).

C $C_{13}H_{12}O$, MW: 184.26. GC-MS: 184 (100%), 183 (40.0%), 169 (20.3%), 167 (14.3%), 165 (44.2%), 153 (9.2%), 115 (14.8%), 82 (9.6%), 73 (14.4%).

D 3'-methyl-[1,1'-biphenyl]-2-ol $C_{13}H_{12}O$, MW: 184.26. GC-MS: 184 (100%), 183 (45.4%), 169 (11.0%), 168 (15.8%), 165 (17.0%), 141 (12.7%), 128 (10.8%), 115 (15.1%), 77 (11.8%), 76 (12.5%).

E 3-methyl-[1,1'-biphenyl]-2-ol $C_{13}H_{12}O$, MW: 184.26. GC-MS: 184 (100%), 183 (28.2%), 169 (64.1%), 168 (14.2%), 165 (18.6%), 141 (17.7%), 115 (21.2%), 91 (18.3%), 82 (12.8%), 77 (13.9%).

F $C_{14}H_{14}O$, MW: 198.26, GC-MS: 198 (66.6%), 184 (93.4%), 183 (100%), 169 (52.1%), 168 (29.8%), 165 (36.0%), 153 (23.7%), 152 (26.5%), 128 (24.2%), 115 (25.9%).

G $C_{14}H_{14}O$, MW: 198.26, GC-MS: 198 (100%), 184 (13.1%), 183 (89.0%), 181 (27.6%), 165 (51.5%), 153 (18.5%), 152 (20.5%), 82 (14.5%), 77 (18.4%), 76 (18.6%).

H 3,3'-dimethyl-[1,1'-biphenyl]-2-ol $C_{14}H_{14}O$, MW: 198.26, GC-MS: 198 (100%), 197 (19.5%), 183 (58.2%), 181 (14.8%), 165 (19.2%), 155 (15.4%), 153 (14.4%), 53 (14.6%), 115 (13.5%), 76 (13.5%).

I: $C_{14}H_{14}O$, MW: 198.26, GC-MS: 198 (100%), 197 (22.2%), 183 (57.5%), 181 (14.8%), 168 (12.3%), 165 (17.5%), 153 (12.9%), 152 (15.4%), 128 (15.2%), 89 (12.7%).

J $C_{14}H_{16}O$, MW: 212.29, GC-MS: 212 (23.8%), 198 (100%), 197 (39.7%), 183 (74.4%), 181 (25.6%), 165 (32.1%), 153 (21.7%), 152 (20.9%), 77 (19.5%), 76 (15.4%).

K $C_{14}H_{16}O$, MW: 212.29, GC-MS: 212 (87.2%), 198 (17.4%), 197 (100%), 183 (13.8%), 182 (22.6%), 181 (14.6%), 165 (13.1%), 153 (15.5%), 152 (15.6%), 115 (15.6%).

L $C_{14}H_{16}O$, MW: 212.29, GC-MS: 212 (100%), 197 (75.1%), 183 (52.2%), 179 (22.0%), 178 (53.1%), 165 (21.9%), 153 (21.7%), 152 (20.8%), 98 (21.3%), 76 (21.5%).

M $C_{14}H_{16}O$, MW: 212.29, GC-MS: 212 (100%), 198 (16.5%), 197 (95.2%), 195 (21.6%), 182 (21.6%), 181 (16.2%), 178 (22.4%), 165 (20.3%), 152 (17.5%), 105 (16.9%).

Figure 10:
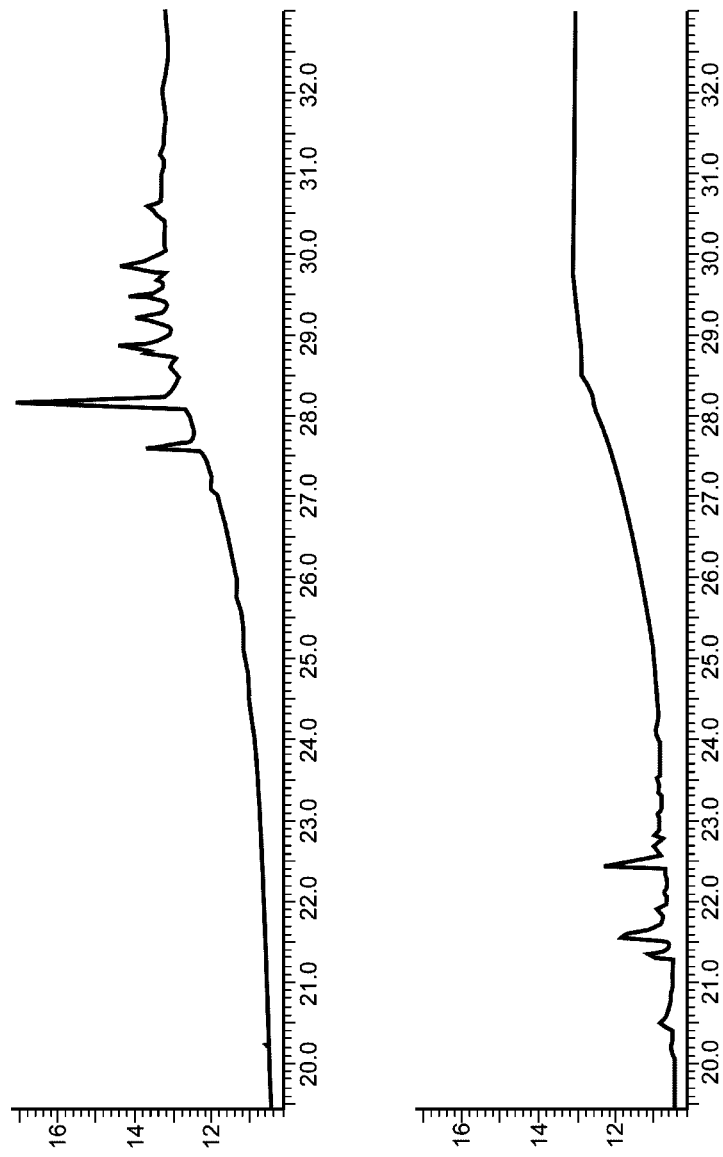
FIG. 10 are GC spectra of mixed sulfones and mixed phenols from a diesel fraction.

FIG. 10 shown the GC spectra of mixed sulfones (top) and mixed phenols (bottom). From the bottom diagram, we can see that there are no sulfones left after the hydrocarbon recovery process.

The method and system of the present invention have been described above and in the attached drawings; however, modifications will be apparent to those of ordinary skill in the art and the scope of protection for the invention is to be defined by the claims that follow.

The invention claimed is:

1. A process for conversion of sulfones in a sulfone-containing hydrocarbon mixture into phenol derivatives of the sulfones, the conversion process comprising:
   mixing one or more alkaline compounds with the sulfone-containing hydrocarbon mixture without a solvent;
   retaining the alkaline compound(s) in contact with the sulfone-containing hydrocarbon mixture at a temperature of 380° C. or less in a reaction mixture for a period of time sufficient to promote reaction of the sulfones in said sulfone-containing hydrocarbon mixture into phenol derivatives of the sulfones.

2. The process as in claim 1 wherein the reaction occurs at ambient pressure.

3. The process as in claim 1 wherein the alkaline compound(s) are retained in contact with the sulfone(s) for a period of about one minute to about sixty minutes.

4. The process as in claim 1, wherein the alkaline compound(s) are retained at a temperature of about 200° C. to 380° C.

5. The process as in claim 1, wherein the sulfones in the sulfone-containing hydrocarbon mixture comprise alkyl substituted benzothiophene sulfones or alkyl substituted dibenzothiophene sulfones.

6. The process as in claim 1, wherein the sulfones in the sulfone-containing hydrocarbon mixture comprise extended conjugation benzothiophene sulfones or extended conjugation dibenzothiophene sulfones.

7. The process as in claim 1, wherein the alkaline compounds comprise individual alkali hydroxide or a mixture of thereof selected from MOH, wherein M=Li$^+$, Na$^+$, K$^+$, Rb$^+$, or Cs$^+$.

8. The process as in claim 1, wherein the alkaline compounds comprise alkali carbonates or a mixture thereof selected from $M_2CO_3$, wherein M=Li$^+$, Na$^+$, K$^+$, Rb$^+$, or Cs$^+$.

9. The process as in claim 1, wherein the alkaline compounds comprise alkaline earth hydroxides or a mixture thereof selected from $M(OH)_2$, wherein M=Mg$^{2+}$, Ca$^{2+}$, Sr$^{2+}$, or Ba$^{2+}$.

10. The process as in claim 1, wherein the alkaline compounds are a mixture of alkali hydroxides, alkali carbonates and alkaline earth hydroxides.

11. The process as in claim 1, further comprising adding a dilute acid solution to neutralize the reaction mixture.

12. The process as in claim 11, wherein the acid solution is acetic acid, hydrochloric acid, sulfuric acid or a mixture thereof.

13. The process as in claim 1, wherein the molar ratio of alkaline compounds to sulfones is in the range of 3/1 to 10/1.

14. The process as in claim 1, wherein the molar ratio of alkaline compounds to sulfones is about 5/1.

15. The process as in claim 1, wherein the alkaline compound is an alkali hydroxide or a mixture containing an alkali hydroxide, the reaction temperature is about 200° C. to 380° C. and the reaction time is about 1 to 60 minutes.

16. The process as in claim 15, wherein the reaction temperature is about 300° C. and the reaction time is about 5 minutes.

17. The process as in claim 1, wherein the alkaline compound is an alkaline earth hydroxide or a mixture containing an alkaline earth hydroxide, the reaction temperature is about 200° C. to 380° C. and the reaction time is 1-60 minutes.

18. The process as in claim 17, wherein the reaction temperature is about 350° C. and the reaction time about 5 to 10 minutes.

19. The process as in claim 1, wherein the alkaline compound is an alkali carbonate or a mixture containing an alkali carbonate, the reaction temperature is about 200° C. to 380° C. and the reaction time is 1-60 minutes.

20. The process as in claim 19, wherein the reaction temperature is about 350° C. and the reaction time is about 5 to 10 minutes.

21. A process for conversion of sulfones in a sulfone-containing hydrocarbon mixture into phenol derivatives of the sulfones, the conversion process comprising:
   mixing one or more alkaline compounds with the sulfone-containing hydrocarbon mixture;
   retaining the alkaline compound(s) in contact with the sulfone-containing hydrocarbon mixture at ambient pressure and at a temperature of 380° C. or less in a reaction mixture for a period of time sufficient to promote reaction of the sulfones in said sulfone-containing hydrocarbon mixture into phenol derivatives of the sulfones.

22. The process as in claim 21 wherein the alkaline compound(s) are incorporated without a solvent.

23. The process as in claim 21 wherein the alkaline compound(s) are retained in contact with the sulfone(s) for a period of about one minute to about sixty minutes.

24. The process as in claim 21, wherein the alkaline compound(s) are retained at a temperature of about 200° C. to 380° C.

25. The process as in claim 21, wherein the sulfones in the sulfone-containing hydrocarbon mixture comprise alkyl substituted benzothiophene sulfones or alkyl substituted dibenzothiophene sulfones.

26. The process as in claim 21, wherein the sulfones in the sulfone-containing hydrocarbon mixture comprise extended conjugation benzothiophene sulfones or extended conjugation dibenzothiophene sulfones.

27. The process as in claim 21, wherein the alkaline compounds comprise individual alkali hydroxide or a mixture of thereof selected from MOH, wherein M=$Li^+$, $Na^+$, $K^+$, $Rb^+$, or $Cs^+$.

28. The process as in claim 21, wherein the alkaline compounds comprise alkali carbonates or a mixture thereof selected from $M_2CO_3$, wherein M=$Li^+$, $Na^+$, $K^+$, $Rb^+$, or $Cs^+$.

29. The process as in claim 21, wherein the alkaline compounds comprise alkaline earth hydroxides or a mixture thereof selected from $M(OH)_2$, wherein M=$Mg^{2+}$, $Ca^{2+}$, $Sr^{2+}$, or $Ba^{2+}$.

30. The process as in claim 21, wherein the alkaline compounds are a mixture of alkali hydroxides, alkali carbonates and alkaline earth hydroxides.

31. The process as in claim 21, further comprising adding a dilute acid solution to neutralize the reaction mixture.

32. The process as in claim 21, wherein the acid solution is acetic acid, hydrochloric acid, sulfuric acid or a mixture thereof.

33. The process as in claim 21, wherein the molar ratio of alkaline compounds to sulfones is in the range of 3/1 to 10/1.

34. The process as in claim 21, wherein the molar ratio of alkaline compounds to sulfones is about 5/1.

35. The process as in claim 21, wherein the alkaline compound is an alkali hydroxide or a mixture containing an alkali hydroxide, the reaction temperature is about 200° C. to 380° C. and the reaction time is about 1 to 60 minutes.

36. The process as in claim 35, wherein the reaction temperature is about 300° C. and the reaction time is about 5 minutes.

37. The process as in claim 21, wherein the alkaline compound is an alkaline earth hydroxide or a mixture containing an alkaline earth hydroxide, the reaction temperature is about 200° C. to 380° C. and the reaction time is 1-60 minutes.

38. The process as in claim 37, wherein the reaction temperature is about 350° C. and the reaction time about 5 to 10 minutes.

39. The process as in claim 21, wherein the alkaline compound is an alkali carbonate or a mixture containing an alkali carbonate, the reaction temperature is about 200° C. to 380° C. and the reaction time is 1-60 minutes.

40. The process as in claim 39, wherein the reaction temperature is about 350° C. and the reaction time about 5 to 10 minutes.

* * * * *